US008463556B2

(12) United States Patent
Kaye

(10) Patent No.: US 8,463,556 B2
(45) Date of Patent: Jun. 11, 2013

(54) SYSTEM AND METHOD FOR RADIOISOTOPE IDENTIFICATION

(75) Inventor: Anthony B. Kaye, Fairfax, VA (US)

(73) Assignee: Exelis Inc., McLean, VA (US)

( * ) Notice: Subject to any disclaimer, the term of this patent is extended or adjusted under 35 U.S.C. 154(b) by 814 days.

(21) Appl. No.: 11/847,602

(22) Filed: Aug. 30, 2007

(65) Prior Publication Data
US 2010/0137148 A1 Jun. 3, 2010

(51) Int. Cl.
G01N 33/48 (2006.01)
G01N 31/00 (2006.01)
G01N 33/50 (2006.01)
G06F 7/60 (2006.01)
G06F 17/10 (2006.01)
A61B 5/00 (2006.01)
G06F 19/00 (2006.01)

(52) U.S. Cl.
CPC .. *A61B 5/00* (2013.01); *G06F 19/34* (2013.01)
USPC ...................... 702/22; 702/19; 702/27; 703/2

(58) Field of Classification Search
USPC ........................................................ 250/336
See application file for complete search history.

(56) References Cited

U.S. PATENT DOCUMENTS 5,369,578 A 11/1994 Roscoe et al.
6,577,697 B2 * 6/2003 Pearcy et al. .................. 376/159

FOREIGN PATENT DOCUMENTS

WO 2007065004 A2 6/2007

OTHER PUBLICATIONS

Koch et al. Bremsstrahlung cross-section formulas and related data. Reviews of Modern Physics, vol. 31, 1959, pp. 920-956.*
Easterbrook DJ. Radiocarbon chronology of late Pleistocene deposits in Northwest Washington. Science, vol. 152, 1966, pp. 764-767.*
Libby WF. Dating by radiocarbon. Accounts of Chemical Research, vol. 5, 1972, pp. 289-295.*
Radioactive Dating, 2009. The Hutchinson Unabridged Encyclopedia with Atlas and Weather Guide. Retrieved online on Jan. 21, 2011 <<http://www.credoreference.com/entry/heliconhe/radiocarbon_dating>> Three pages.*
Cross Section, 2001. Cambers 21$^{st}$ Century Dictionary. Retrieved online on Jan. 24, 2011 <<http://www.credoreference.com/entry/chambdict/cross_section>> One page.*
Higham T. Radiocarbon web-info, 1999, Five pages. Retrieved online on Jan. 24, 2011 from <<http://www.c14dating.com>> and <<http://www.c14dating.com/agecalc.html>>.*

(Continued)

*Primary Examiner* — Russell S Negin
(74) *Attorney, Agent, or Firm* — Edell, Shapiro & Finnan, LLC

(57) ABSTRACT

A system and method are providing for analyzing radiation signature data (i.e., spectral data) produced by a detector device against stored data representing the computed interaction of known radioisotopic spectra with a representative cross section for each of a small number of material groups. Each material group comprises materials expected to be in a detection path of the detector and which exhibit similar cross sections. Comparative analysis is made of the spectral data received from the detector for threat materials to determine whether the spectral data indicates presence of a threat material in the interrogated space. The system and method is not limited to any particular detector type, and may be used with any detector that produces spectral data.

25 Claims, 6 Drawing Sheets

OTHER PUBLICATIONS

Definition of semiconductor. Hargrave's Communications Dictionary, Wiley, 2001, one page. Obtained online on Jun. 24, 2011 from <<http://www.credoreference.com.entry.hargravecomms/semiconductor>>.*

Victor Orphan, et al., "Advanced Cargo Container Scanning Technology Development," Science Applications International Corporation, San Diego, California 92127, 7th Marine Transportation System Research and Technology Conference, Washington, D.C., Nov. 16-17, 2004.

Berkeley Nucleonics Corporation (BNC), Model 1703MB/GNB Gamma/Gamma-Neutron Pager, Product Information Brochure, Jan. 2007.

Roemer K. et al., "Simulation of Template Spectra for Scintillator Based Radionuclide Identification Devices Using GEANT4," IEEE Nuclear Science Symposium Conference Record—2006 IEEE Nuclear Science Symposium—Conference Record 2007 Institute of Electrical and Electronics Engineers Inc., US, vol. 1, Oct. 29, 2006, pp. 247-252.

Estep R. J. et al., "The Multiple Isotope Material Basis Set (MIMBS) Method for Isotope Identification with Low-and Medium-Resolution Gamma-Ray Detectors," Journal of Radioanalytical and Nuclear Chemistry, Kluwer Academic Publishers, D0, vol. 276, No. 3, May 2, 2008, pp. 737-741.

Gardner R. P. et al., "Status of Software for PGNAA Bulk Analysis by the Monte Carlo Library Least-Squares (MCLLS) Approach," Journal of Radioanalytical and Nuclear Chemistry, Kluwer Academic Publishers, D0, vol. 264, No. 1, Mar. 1, 2005, pp. 221-228.

Magistris M. et al., "The Fingerprint Method for Characterization of Radioactive Waste in Hadron Accelerators," Nuclear Instruments and Methods in Physics Research, Section—A: Accelerators, Spectrometers, Detectors and Associated Equipment, Elsevier, Amsterdam, NL, vol. 591, No. 2, Jun. 21, 2008, pp. 343-352.

European Search Report Corresponding to European Application No. 08163023.8; dated Jan. 19, 2009.

Will H. Hill et al., "Experimental Verification of a Hand Held Electronically-Collimated Radiation Detector," Nuclear Science Symposium Conference Record, 2007; NSS '07; IEEE, IEEE, PI, Oct. 1, 2007, pp. 3792-3797, XP031206432.

S. Agostinelli et al., "GEANT4—a simulation toolkit," Nuclear Instruments and Methods in Physics Research, Section—A: Accelerators, Spectrometers, Detectors and Associated Equipment, Elsevier, Amsterdam, NL, vol. 506, No. 3, Jul. 1, 2003, pp. 250-303, XP004431463.

A. L. Nichols, "Decay Data: Review of Measurements, Evaluations and Compilations," Applied Radiation and Isotopes, Elsevier, Oxford, GB, vol. 55, No. 1, Jul. 1, 2001, pp. 23-70, XP004234045.

R. E. Abdel-Aal et al., "Determination of Radioisotopes in Gamma-Ray Spectroscopy Using Abductive Machine Learning," Nuclear Instruments & Methods in Physics Research, Section—A: Accelerators, Spectrometers, Detectors and Associated Equipment, Elsevier, Amsterdam, NL, vol. 391, No. 2, Jun. 1, 1997, pp. 275-288, XP004084518.

Laurus Systems, rad-ID™ Hand-Held Isotope Identifier for Accurate In-Field Analysis, Product Information Brochure, Feb. 2, 2004.

* cited by examiner

SYSTEM AND METHOD FOR RADIOISOTOPE IDENTIFICATION

BACKGROUND OF THE INVENTION

The present invention is directed to detecting radioactive materials that may be inside containers or otherwise shielded.

Efforts are underway to develop technologies capable of detecting the presence of materials that may be placed inside a container for purposes of transporting the material to a destination. Examples of harmful materials that may be most important to identify are radioactive, explosive, biological, and/or chemical agents.

Current radioisotopic identification is based upon peak-finding and pattern-matching algorithms. These techniques may be sufficient in the laboratory and in some industrial applications (e.g., in commercial nuclear power reactors), but they fall short in attempts to detect shielded radioisotopes in transit, largely because current algorithms do not sufficiently account for the interaction between the emitted radiation and the surrounding matter. The principal difficulties in developing isotopic identification software are twofold.

First, generally speaking, the detected spectra of shielded radioisotopes are weak and potentially buried in noise from, for example, natural background radiation and radiation emanating from nearby naturally radioactive legal sources (e.g., bananas, cat litter, medical isotopes). These weak spectra are difficult to analyze, since one of the main restrictive conditions of research in this area is that the flow of commerce not be unduly delayed by the detection process. Therefore, the longer detector integration times that would be used to obtain stronger signals are not practical in real-world applications. However, even with stronger signals, it is not clear that shielded radioisotopes, including some considered to be dangerous, can be located.

Second, the detection and identification of particular radioisotopes depends upon the interaction of the radiation with its surroundings. This environmental interaction is generally unknown and consequently is one of the most difficult aspects of the radioisotope detection and identification scenario. Analysis techniques that are currently used ignore the impact of surrounding materials in attempting to detect and identify threat radioisotope materials in a container or an otherwise shielded environment.

What is needed is a technique to analyze the radiation signature data (in the form of a spectrum) from any available detector device in order to rapidly and accurately determine the presence of a threat material in a space.

SUMMARY OF THE INVENTION

Briefly, a system and method are providing for analyzing spectral data produced by a detector device to determine presence of one or more threat materials of interest in a space that is monitored by the detector. Materials expected to be in a detection path of the detector, including threat materials of interest and non-threat materials, are grouped into one of a plurality of material groups based on similarities in their cross sections. Data describing a representative energy versus cross section curve for each material group is selected from cross sections of individual materials in the respective material group. The interaction of each material of interest (sources) with one or more of the material groups (shielding material groups) is computed using the representative energy versus cross section curve for the respective material groups to produce computational spectral data for the material of interest. Thus, a library of spectral data is built from the individual spectral data computed for each source/shield material(s) combination. The spectral data produced by the detector is analyzed against the library of computational spectral data to determine presence of a threat material in the space.

DETAILED DESCRIPTION

Radiation interacts with matter in a well-known way. The intensity of radiation, I, from a monochromatic photon source along any given path as a fraction of its original intensity, $I_0$, is given by the relationship:

$$\frac{I}{I_0} = e^{-\rho \sigma x},$$

in which the particles (in the context of the present invention, either photons or neutrons) travel through a single material, having a density $\rho$, a total cross section for interaction $\sigma$ (that depends not only upon the specific particle, but on the energy E of the particle when it interacts with the material), and the path length x through which the particle travels. A more generalized relationship can be written for interaction with multiple materials. Therefore, as radiation travels through various materials (including air), the detected spectrum (signature) is likely to be weakened (reduced in amplitude) and the various peaks in the spectrum are likely to be shifted in energy. Each spectral feature may be affected differently from the rest. Therefore, the identification of specific radioisotopes is not only a matter of signal-to-noise conditions, but also involves understanding, modeling, and coding the interaction of radiation with matter in a way from which the end user will benefit.

While these various interactions are, by and large, understood and can be modeled and predicted very well (using, e.g., Monte Carlo computer software known in the art as "MCNP" or "PENELOPE"), they require that the entire geometry (including material properties) be specified. Once the geometry is defined, these software algorithms use Monte Carlo techniques and massive cross-section libraries (e.g., the "ENDF-VI" libraries distributed by, e.g., the National Nuclear Data Center, the Radiation Safety Information Computational Center, and the Nuclear Reaction Data Centers; the libraries can require the use of large amounts of computer storage space) to simulate the specified problem. If all of the materials, their physical properties (e.g., density) and specific chemical compositions, and their respective location(s) and geometric configuration(s) in the problem are not well defined, these software algorithms become less than optimal.

According to the present invention, an isotope identification algorithm is provided that allows a user to interrogate spectral data (provided from any detector heretofore known or hereinafter developed) and make well-informed operational decisions based upon the results. This algorithm takes into account the interaction between the radiation and surrounding matter. In physics, the concept of a cross section is used to express the likelihood of interaction between particles.

Figure 1:
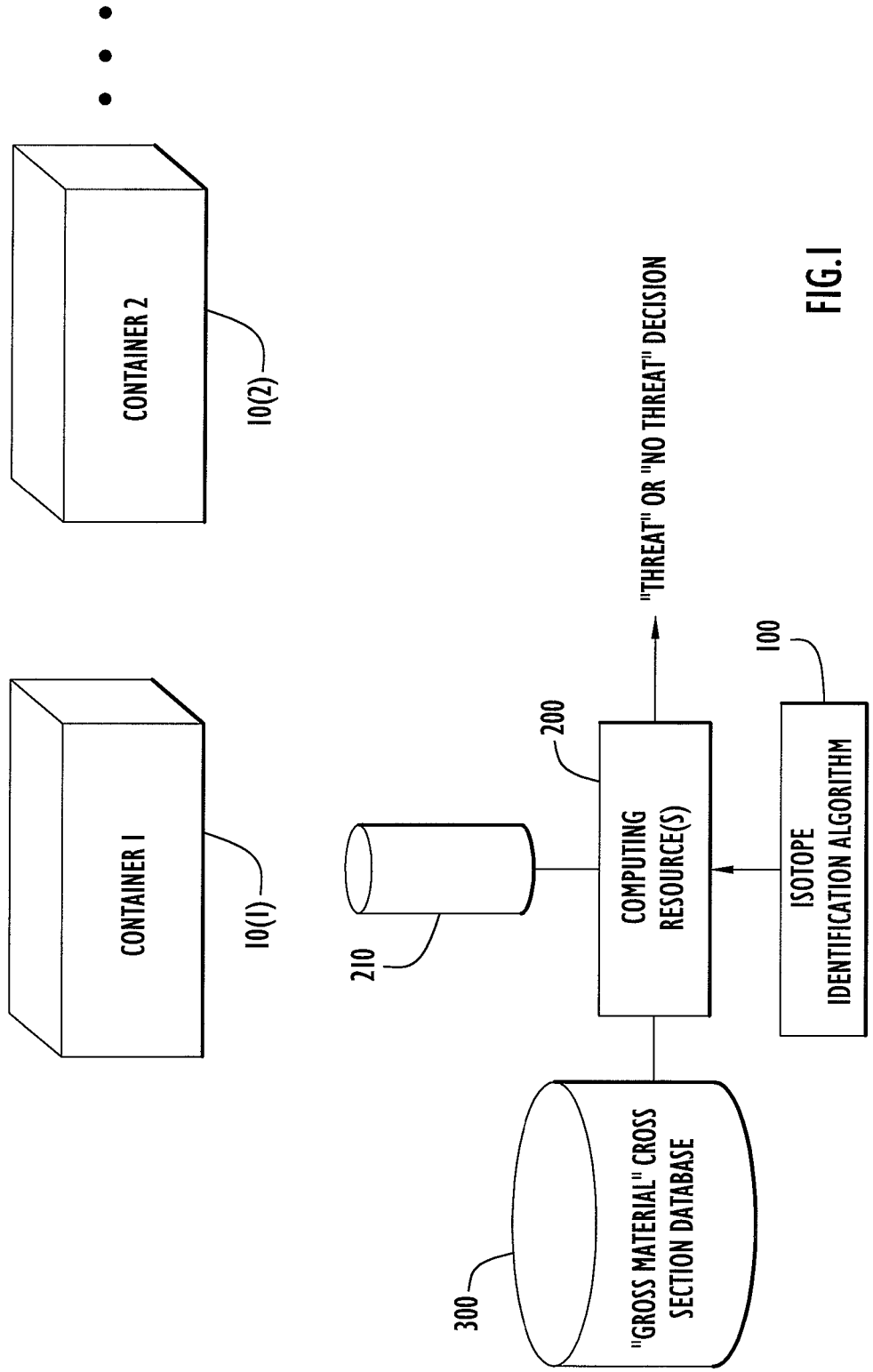
FIG. 1 is a block diagram showing a container scanning system according to an embodiment of the invention.

Referring first to FIG. 1, one possible operating environment is shown for the isotope identification algorithm according to the present invention. The algorithm, indicated by reference numeral 100, may be embodied by computer software, is executed by one or more computing resources 200. Execution of the algorithm 100 involves use of cross section data, determined a priori, stored in a database hereinafter referred to as a "gross material" cross section database 300. The computing resource(s) 200 operates on data generated by a detector 210 that interrogates a substantially contained space. The algorithm 100 is not limited to use with any particular type of detector 210; nevertheless, examples of such detectors 210 are those based upon silicon, sodium iodide, high-purity germanium, cadmium zinc telluride, thorium tetrabromide, lanthanide or actinide halides, or any derivative thereof, or those based on physical "gating" or time-of-flight. In general, the detector 210 may be any detector or detection system that produces spectra. The computing resource(s) 200 may be a computer that operates on software, as mentioned above, or may be comprise an application specific integrated circuit, programmable logic circuits, digital signal processor(s) programmed with suitable firmware, etc.

The detector 210 is positioned to detect radiation associated with containers 10(1), 10(2), ..., or other body that is to be scanned or examined to determine whether it contains a radioactive source material of interest, i.e., a threat material. The term "container" is meant to include, without limitation, shipping containers, trucks, rail cars, crates, as well as smaller sized containers such as hand-held containers. The detector 210 is positioned with respect to the containers 10(1), 10(2), etc., as it would normally would during operation; no special placement or configuration of the detector 210 is required to perform the techniques described herein. The computing resource(s) 200 capture the spectral data produced by the detector 210 and executes the algorithm 100 on the spectral data against a library of spectral data derived from the database 300 to determine whether or not there is a radioactive threat material in each container 10(1), 10(2), etc. In addition, algorithm 100 may identify the specific threat material. Thus, the computing resource(s) 200 outputs an indication of whether or not a threat material is present in a container and (potentially) information identifying the specific threat material(s). The library of spectral data (also called library spectra) is computed according to the techniques described hereinafter in connection with FIG. 3.

Figure 2:
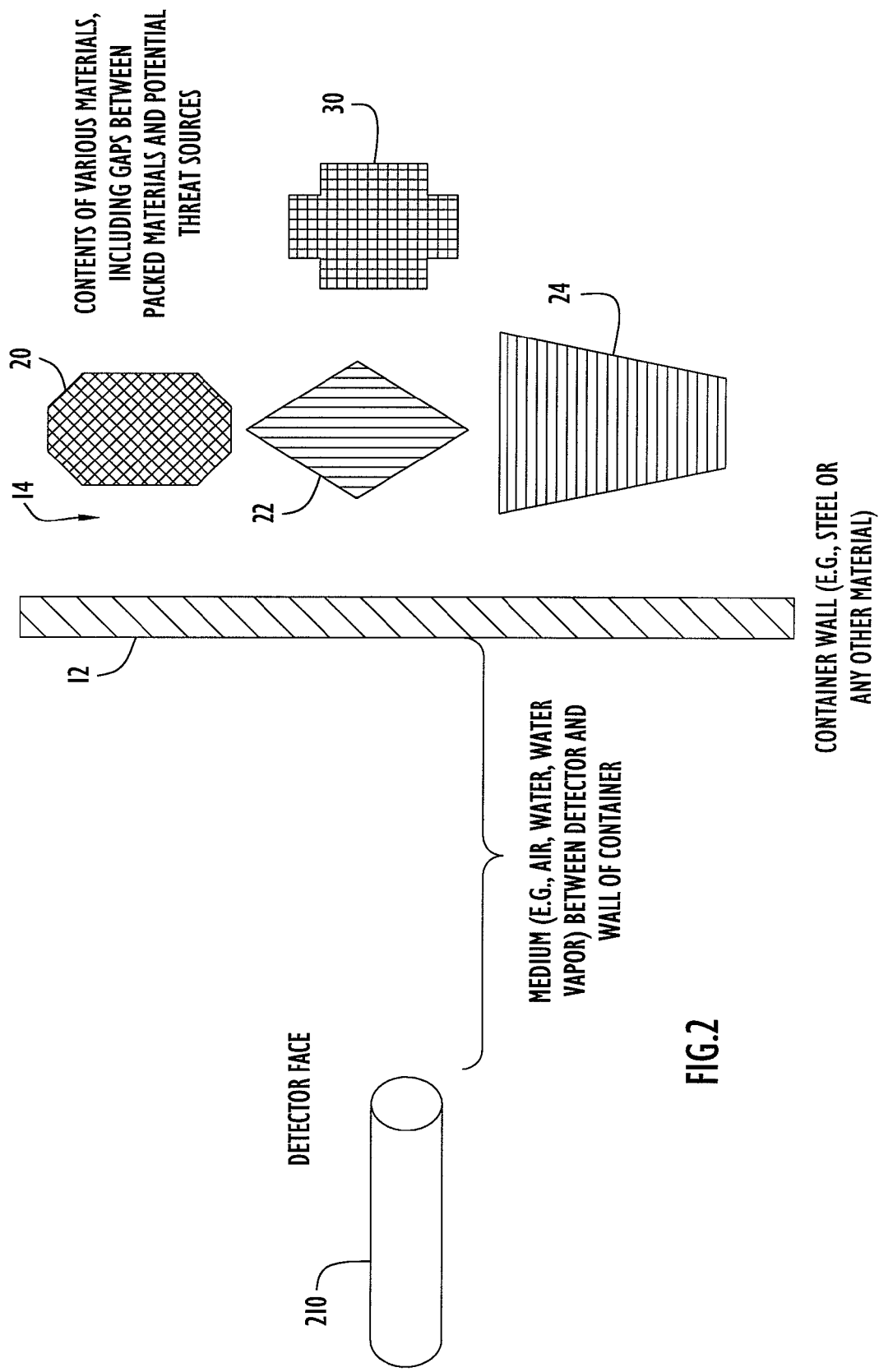
FIG. 2 is a schematic diagram illustrating examples of commonly-encountered materials that the detector must sort through according to the embodiments of the present invention.

Turning now to FIG. 2, the nature of the problem that the algorithm 100 addresses is described in more detail. The detector 210 may be positioned at some separation distance from a wall 12 of a container 10(1), 10(2), etc., as it would nominally be placed during normal operation. The wall 12 may also represent some shielding device or barrier between the detector 210 and a (finite and bounded) space 14 that is to be scanned for the presence and identification of harmful radioactive materials. It should be understood that there may several walls, spaced or not spaced from each other, between the detector 210 and the space 14. There may be some applications where there is no wall, in which cases the wall need not be taken into consideration. The techniques described herein work in applications both with and without a wall 12. In the example shown in FIG. 2, there are objects 20, 22, and 24 in the space 14 that do not contain or embody a threat material, whereas object 30 contains or embodies a harmful radioisotope threat material to be detected and identified. The objects 20, 22, 24, and 30 may packed tightly or loosely in any configuration in the space 14. The medium between the detector and the wall 14 may be air, water, water vapor, or any combination of these or other materials.

According to the present invention, cross section data of the "gross materials" is used for materials that are expected to be in the detection path of the detector. This includes materials that are potentially in the space 14, in the wall 12, and in the medium between the wall 12 and the detector 210. In one embodiment, photon cross section data alone is used. In another embodiment, neutron cross section data is used. In still another embodiment, both photon cross section data and neutron cross section data for the expected materials are used.

Figure 3:
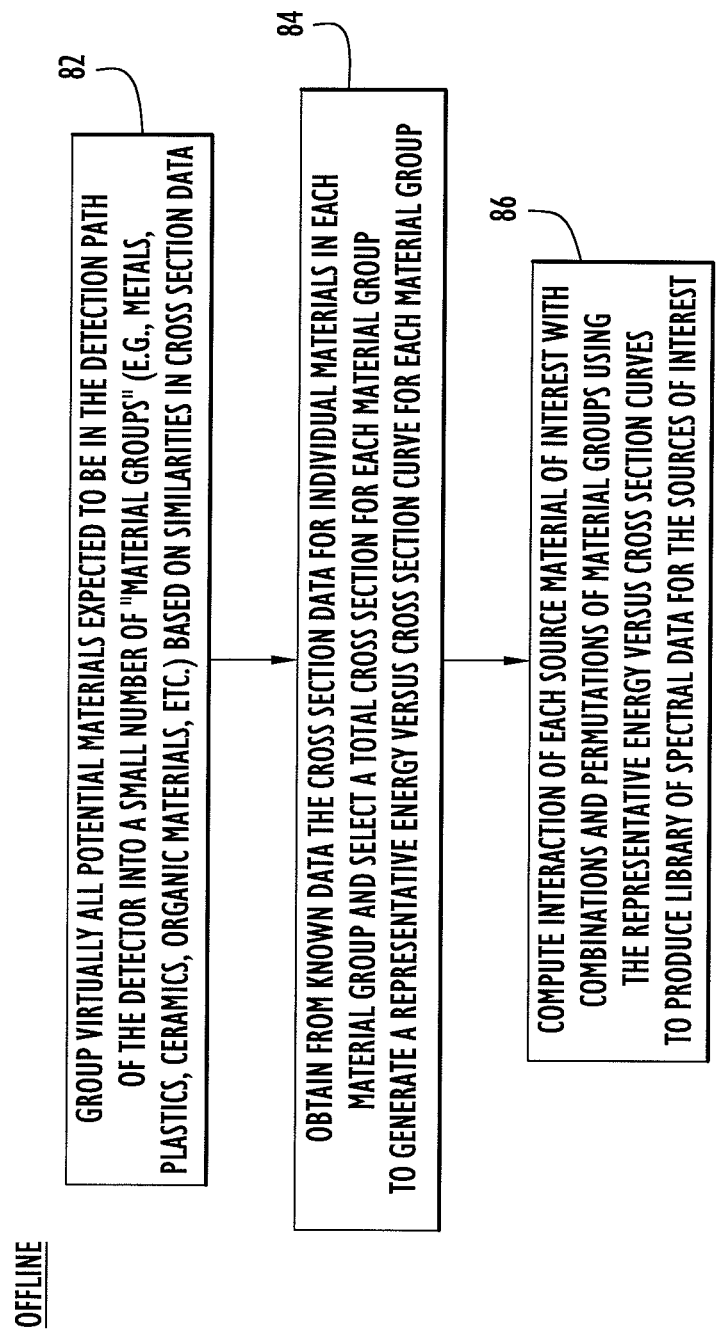
FIG. 3 is a flow chart illustrating an offline data gathering and analysis stage to produce data used in the identification technique according to an embodiment of the present invention.
Figure 4:
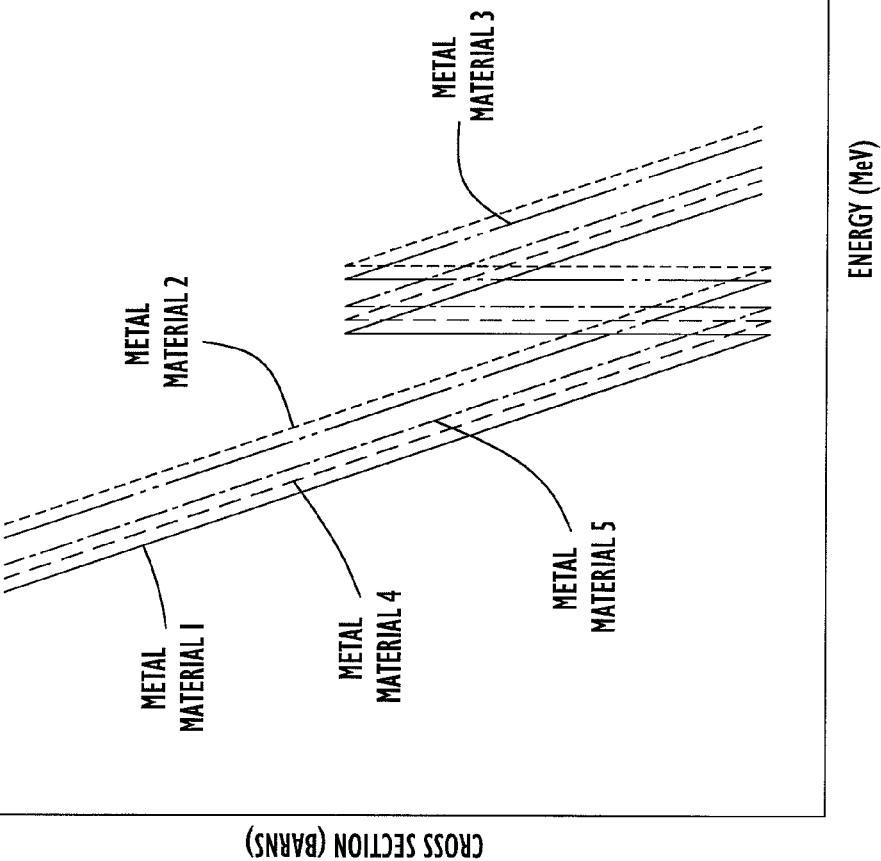
FIG. 4 illustrates plots of photon cross section as a function of energy for a metals material group used as part of the separation and identification process of the present invention.

Reference is now made to FIG. 3 which shows a flow chart of a process 80 that is executed off-line prior to execution of the algorithm 100 in order to generate a library of spectral data against which the spectral data output by the detector 210 is analyzed. The process 80 begins at 82 by grouping all the materials expected to be in the detection path of the detector into a small (less than or equal to 10) number of so-called "gross material groups" based on similarities in their cross section data. In general, the number of material groups is substantially less than the number of materials in all of the groups combined. There is a trade-off between having so many material groups that the advantages of the techniques described are not achieved versus having too few material groups such that the algorithm 100 is not reliably accurate. The materials groups in the detection path of the detector are also referred to herein as "shielding material groups". For example, a first material group may be metals, a second material group may be ceramics, a third material group may be organic materials, and so on. All materials that are considered for purposes of the algorithm 100 are classified into one of these material groups, including materials that are not threat source materials of interest and materials that are threat source materials of interest. Next, at 84, a total cross section is selected for each material group using known or available cross section data for each material in that group, to produce a representative energy versus cross section curve for that group of materials. For example, FIG. 4 shows portions of plots of total photon cross section data (as a function of energy) for 5 types of metal materials. The similarity of the shape of the photon cross section plots for these metal materials is quite evident from FIG. 4. Thus, these metal materials would be grouped into the same material group, e.g., designated metals. To reiterate, at 82 the cross section data for a collection of materials is evaluated and the materials are group based on cross section similarity. Once a group is established, at 84, one of the materials in the group is selected as the "representative" material and the cross section versus energy curve for that material is used as the "representative" cross section versus energy curve for that material group. The representative material for a material group is also referred to herein as the "gross material". FIG. 4 shows plots of cross section data for only 5 types of metal materials; however it should be understood that numerous metal materials may have similar plots of photon cross section data. Similarly, materials may be classified by their neutron cross section data (as a function of energy). Thus, in one embodiment, materials may be grouped into one or both of photon-specific material groups and into neutron-specific material groups.

Next, at 86, for each source material of interest (i.e., each radioisotope), computations are made that compute the interaction of each source with one or more of the material groups in various combinations and permutations (order) using the data for the representative energy versus cross section curves for the material groups. For example, if uranium is a source material of interest, then computations are made that model the interaction of uranium with a desired one or more (in various combinations and permutations) of the material groups using the representative energy versus cross section curves for the respective material groups, to produce computational spectral data for uranium as would be detected by a detector in the presence of one or more of the material groups in the various combinations and permutations. In these computations, the effects of electron transport are taken into consideration (whether for photon cross section or neutron cross section) using any of the known computation techniques for electron transport models, such as MCNP and PENELOPE. These computations are made for each source of interest and the resulting spectral data is stored to produce a library of spectral data for the sources of interest.

Figure 5:
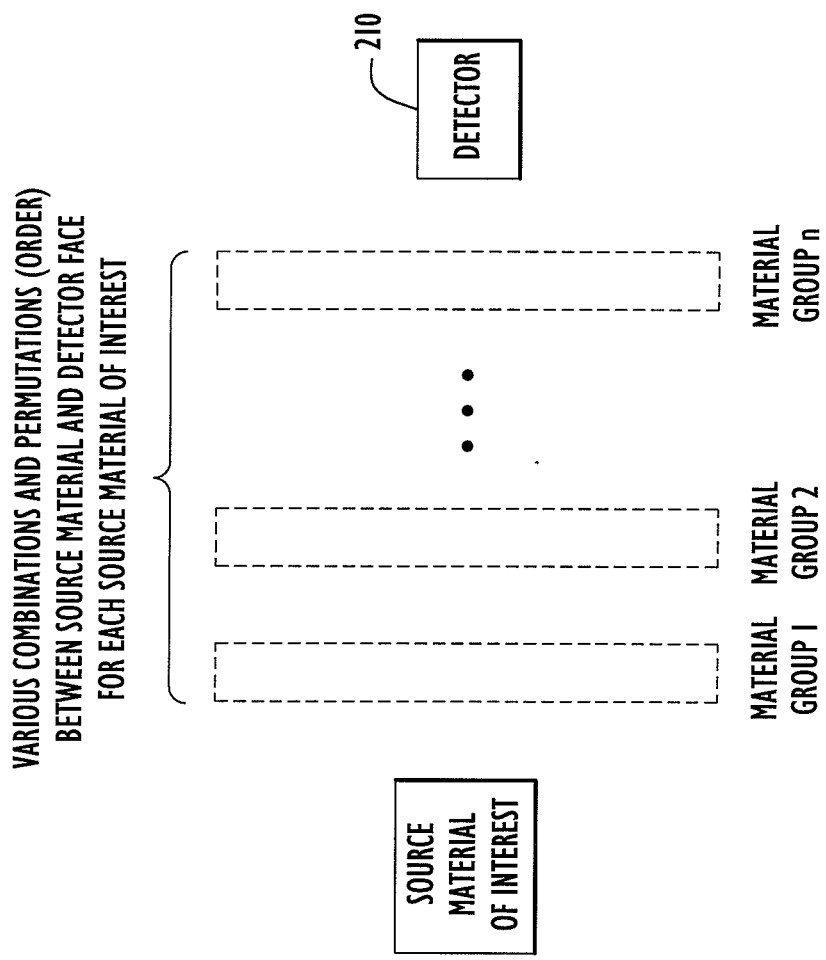
FIG. 5 is a diagram depicting a computation made during the process depicted in FIG. 3.

FIG. 5 graphically depicts what the computations at 86 are modeling. Specifically, for each source material of interest (whose presence is to be detected in the space 14), the interaction computations at 86 model the spectral data that a detector 210 would produce if a source material of interest is in the space together with one or more of the material groups, in various combinations and permutations between the source material of interest and the detector 210. This computation is performed for each source of material of interest. FIG. 5 is simplified to illustrate this idea, and shows generic geometry and combinations for each of the various materials that may be in the detector path. In this way, the various spatial dependencies of the source spectra response to its environment can be incorporated into the database 300.

Figure 6:
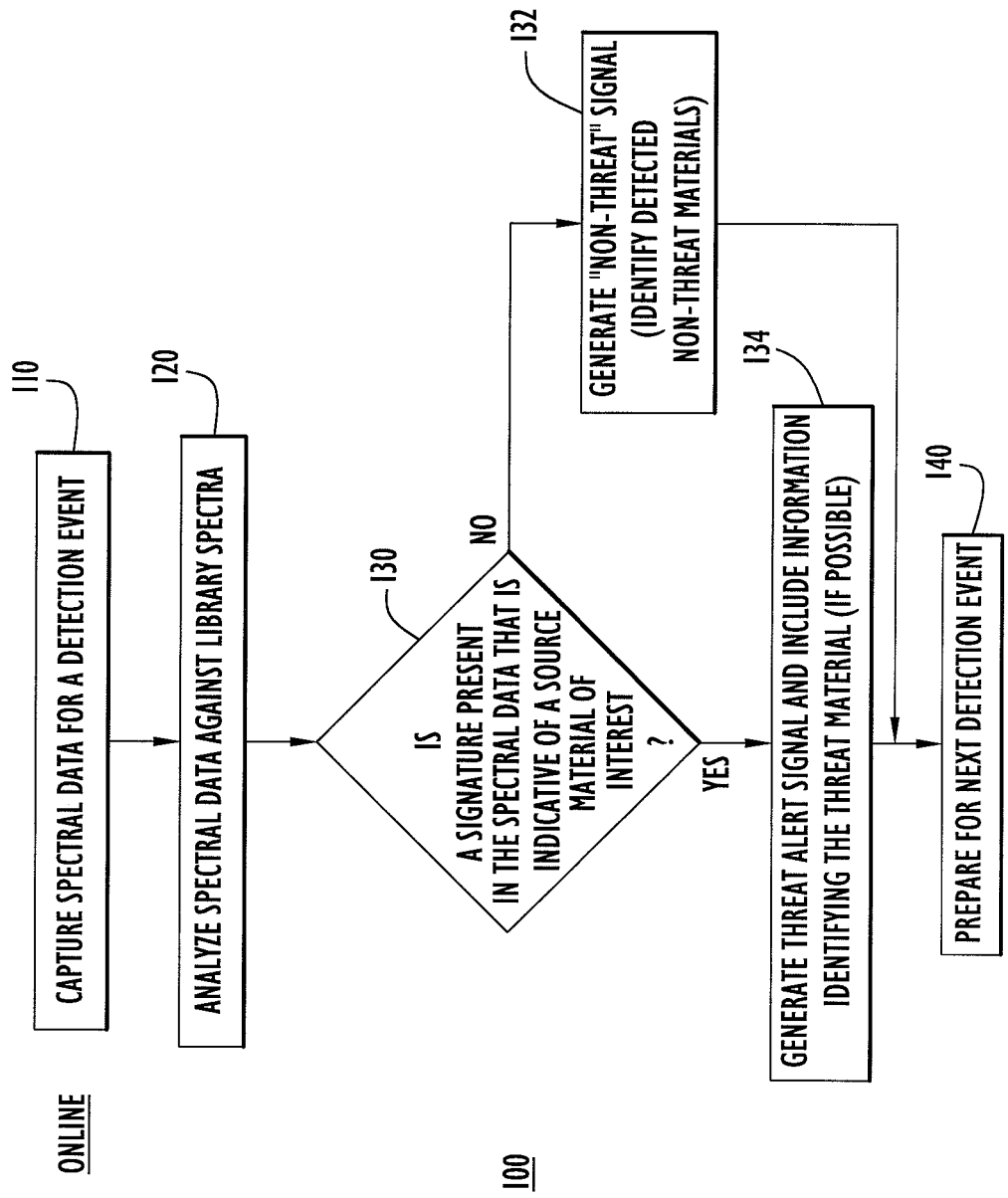
FIG. 6 is a flow chart illustrating the identification technique according to an embodiment of the present invention.

Turning to the flow chart shown in FIG. 6, the algorithm 100 is now described in detail. FIG. 6 shows that the functions in this flow chart are performed "on-line" and this is intended to indicate that these are the functions performed after the database 300 has been populated with the library computational spectral data and after a detection event has been performed. At 110, the spectral data generated by the detector during a detection event is captured. Next, at 120, the spectral data is analyzed against the library of spectral data produced as described above in conjunction with FIG. 3, in order to separate cross section patterns of commonly-encountered materials from cross section patterns associated with threat materials, and thereby determine whether the spectral data output by the detector indicates presence of a threat material, and to identify that threat material. This analysis may involve using any spectral pattern matching algorithm now known or hereinafter developed to determine the presence of, and identify, a threat material based on the spectral data output by the detector.

At 130, it is determined whether a signature is present in the signature data that is indicative of the presence of a threat material in the space 14 based on the analysis performed at 120. If so, the process continues to 134 and if not the process continues to 132. At 132, a non-threat signal or indication is generated together with information identifying the non-threat radioactive material that has been detected (if possible), or no signal or alert is generated. At 134, a threat alert signal is generated together with information identifying the threat material that has been detected (if possible). A user may then choose to more thoroughly inspect the container or other body that has been scanned to locate and isolate the threat material. At 140, preparations are made for the next detection event, i.e., scanning of another container or another portion of a body of interest.

The results at 132 and 134 may be displayed within a running application on the computing resources 200 (FIG. 1) or sent to other hardware to provide an alert. Further outputs may comprise error measures and other auxiliary information such as interactive plots, images, surfaces, or other customized visualizations.

The software that implements the algorithm 100 may be written in any suitable computer language. In one example, it is written using the Interactive Data Language (IDL) and the software environment known as ENVI, both of which are marketed by ITT Corporation. ENVI is written in IDL and is the de facto standard for the processing, exploitation, and analysis of multi-spectral and hyper-spectral datasets. The software for the algorithm 100 may be implemented as a "plug-in" to the ENVI software package, but may be implemented using other techniques to allow its incorporation into a larger system (e.g., as part of a detector system).

The system and methods described herein may be embodied in other specific forms without departing from the spirit or essential characteristics thereof. The foregoing embodiments are therefore to be considered in all respects illustrative and not meant to be limiting.

What is claimed is:

1. A method for analyzing spectral data produced by a detector that interrogates a substantially contained space for presence of one or more radioactive materials of interest, comprising:

grouping materials that could be in a detection path of the detector into one of a plurality of material groups by evaluating energy versus photon cross section and/or energy versus neutron cross section of the materials and such that the plurality of material groups are representative of all materials that could be in the detection path of the detector, and wherein a cross section of a material is a likelihood of interaction between radiation and particles of the material;

selecting data describing a representative energy versus cross section curve for each material group from cross sections of individual materials in the respective material group;

at a computing device, computing interactions of each radioactive material of interest with the material groups using the representative energy versus cross section curve for each material group to produce spectral data for the radioactive material of interest;

at a computing device, generating a library of spectral data comprising the spectral data computed for each radioactive material of interest;

storing the library of spectral data in a data storage device;

detecting radiation from the space with the detector and producing spectral data with the detector; and at a computing device, analyzing the spectral data produced by the detector against the library of spectral data to determine presence of a radioactive material of interest in the space.

2. The method of claim 1, wherein computing comprises computing interaction of each radioactive material of interest with various combinations and permutations of the material groups.

3. The method of claim 1, wherein computing further comprises computing effects of electron transport in the interaction of each radioactive material of interest with the one or more of the material groups.

4. The method of claim 1, and further comprising identifying a radioactive material of interest determined to present in the space based on said analyzing.

5. The method of claim 1, wherein grouping comprises grouping materials into one of a number of material groups based on similarities in both photon cross section and neutron cross section, wherein the number of material groups is substantially less than the number of materials in all of the material groups combined.

6. The method of claim 5, wherein the number of material groups is less than or equal to ten.

7. The method of claim 1, wherein grouping comprises grouping materials based on similarities in shapes of curves describing energy versus photon cross section and/or energy versus neutron cross section of the materials.

8. A method for determining whether a radioactive material of interest is present in a space from spectral data produced by a detector that interrogates the space, comprising:
   storing in a data storage device a library of spectral data representing interactions of radioactive materials of interest with each of a plurality of groups of materials using data describing a representative energy versus cross section curve for each of the plurality of groups of materials, wherein the plurality of material groups are representative of all materials that could be in a detection path of the detector, and wherein the materials are grouped by evaluating energy versus photon cross section and/or energy versus neutron cross section of the materials, and a cross section of a material is a likelihood of interaction between radiation and particles of the material;
   detecting radiation from the space with the detector and producing spectral data with the detector; and
   at a computing device, analyzing the spectral data from the detector against the library of spectral data to determine whether a radioactive material of interest is present in the space.

9. The method of claim 8, and further comprising selecting data describing the representative energy versus cross section curve for each material group from cross sections of individual materials in the respective material group, and computing interaction of each radioactive material of interest with the one or more of the material groups using the representative energy versus cross section curve for the respective material groups to produce the library of spectral data.

10. The method of claim 9, wherein computing the interaction of each radioactive material of interest comprises computing interaction of each radioactive material of interest with various combinations and permutations of the material groups.

11. The method of claim 10, wherein computing the interaction of each radioactive material of interest further comprises computing effects of electron transport in the interaction of each radioactive material of interest with one or more of the material groups.

12. The method of claim 8, and further comprising identifying a radioactive material of interest determined to present in the space based on said analyzing.

13. The method of claim 8, wherein a number of material groups is substantially less than the number of materials in all of the material groups combined.

14. The method of claim 8, wherein a number of materials groups is less than or equal to ten.

15. The method of claim 8, wherein the materials are grouped based on similarities in shapes of curves describing energy versus photon cross section and/or energy versus neutron cross section of the materials.

16. A system for determining the presence of a radioactive material of interest in a space based on spectral data produced by a detector that interrogates the space, comprising:
   a detector configured to detect radiation from the space and to produce spectral data from the detected radiation;
   a data storage device that is configured to store a library of spectral data representing interactions of radioactive materials of interest with each of a plurality of groups of materials using data describing a representative energy versus cross section curve for each of the plurality of groups of materials, wherein the plurality of material groups are representative of all materials that could be in a detection path of the detector and the materials are grouped by evaluating energy versus photon cross section and/or energy versus neutron cross section of the materials, and a cross section of a material is a likelihood of interaction between radiation and particles of the material; and
   a computational resource coupled to the data storage, wherein the computational resource is configured to analyze the spectral data against the library of spectral data to determine whether the spectral data indicates presence of a radioactive material of interest in the space wherein the computational resource is configured to analyze spectral data gathered from the detector against the library of spectral data stored in the data storage device.

17. The system of claim 16, wherein the data storage device is configured to store the library of spectral data that is derived from computing interactions of each radioactive material of interest with one or more of the material groups using data describing the representative energy versus cross section curve for each material group.

18. The system of claim 16, wherein the computational resource is further configured to identify a radioactive material of interest determined to be present in the space.

19. The system of claim 16, wherein data storage device is configured to store spectral data for materials that are grouped based on similarities in shapes of curves describing energy versus photon cross section and/or energy versus neutron cross section of the materials.

20. A non-transitory computer readable medium that stores instructions which, when executed by a computer, cause the computer to:
   receive spectral data output from a detector that detects radiation from a space;
   determine whether a radioactive material of interest is present in space from the spectral data produced by the detector by analyzing the spectral data against a library of spectral data representing interactions of radioactive materials of interest with each of a plurality of groups of materials using data describing a representative energy versus cross section curve for each of the plurality of groups of materials, wherein the plurality of material groups are representative of all materials that could be in a detection path of the detector, the materials are grouped by evaluating energy versus photon cross section and/or energy versus neutron cross section, and a cross section of a material is a likelihood of interaction between radiation and particles of the material.

21. The non-transitory computer readable medium of claim 20, and further comprising instructions that, when executed by a computer, cause the computer to select data for the representative energy versus cross section curve for each material group from cross sections of individual materials in the respective material group, and to compute interaction of each radioactive material of interest with the material groups using the representative energy versus cross section curve for the respective material groups to produce the library of spectral data.

22. The non-transitory computer readable medium of claim 21, wherein the instructions that cause the computer to compute the interaction comprises instructions that cause the computer to compute the interaction of each radioactive material of interest with various combinations and permutations of the material groups.

23. The non-transitory computer readable medium of claim 22, wherein the instructions that cause the computer to compute the interaction comprises instructions that cause the computer to further compute effects of electron transport in the interaction of each radioactive material of interest with one or more of the material groups.

24. The non-transitory computer readable medium of claim 20, and further comprising instructions that cause a computer to identify a radioactive material of interest determined to present in the space.

25. The non-transitory computer readable medium of claim 20, wherein the instructions operable to determine comprise instructions operable to group the materials based on similarities in shapes of curves describing energy versus photon cross section and/or energy versus neutron cross section of the materials.

* * * * *